United States Patent
Higashi et al.

(10) Patent No.: US 11,198,670 B2
(45) Date of Patent: Dec. 14, 2021

(54) HYDROCARBON-CONTAINING CARBOXYLIC ACID, HYDROCARBON-CONTAINING SULFONIC ACID, HYDROCARBON-CONTAINING SULFURIC ACID ESTER OR SALT THEREOF, AND SURFACTANT

(71) Applicant: DAIKIN INDUSTRIES, LTD., Osaka (JP)

(72) Inventors: Masahiro Higashi, Osaka (JP); Satoru Yoneda, Osaka (JP); Akiyoshi Yamauchi, Osaka (JP); Sumi Ishihara, Osaka (JP); Yosuke Kishikawa, Osaka (JP); Hirokazu Aoyama, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 16/338,374

(22) PCT Filed: Sep. 29, 2017

(86) PCT No.: PCT/JP2017/035372
§ 371 (c)(1),
(2) Date: Mar. 29, 2019

(87) PCT Pub. No.: WO2018/062450
PCT Pub. Date: Apr. 5, 2018

(65) Prior Publication Data
US 2020/0024222 A1  Jan. 23, 2020

(30) Foreign Application Priority Data

Sep. 30, 2016 (JP) .............................. JP2016-195062
Mar. 31, 2017 (JP) .............................. JP2017-073087

(51) Int. Cl.
| | |
|---|---|
| *C07C 235/06* | (2006.01) |
| *C07C 69/67* | (2006.01) |
| *C07C 305/10* | (2006.01) |
| *C07C 309/13* | (2006.01) |
| *C07C 69/34* | (2006.01) |
| *C07C 235/12* | (2006.01) |

(52) U.S. Cl.
CPC .......... *C07C 235/06* (2013.01); *C07C 69/34* (2013.01); *C07C 69/67* (2013.01); *C07C 235/12* (2013.01); *C07C 305/10* (2013.01); *C07C 309/13* (2013.01)

(58) Field of Classification Search
CPC ....... C07C 69/34; C07C 69/67; C07C 69/716; C07C 235/06; C07C 305/10; C07C 309/13
See application file for complete search history.

(56) References Cited

U.S. PATENT DOCUMENTS

| | | | |
|---|---|---|---|
| 4,627,938 A * | 12/1986 | Dean ......................... | C08F 4/04 |
| | | | 540/473 |
| 5,028,516 A | 7/1991 | Mukunoki et al. | |
| 9,683,123 B2 * | 6/2017 | Cho ......................... | C07C 57/13 |
| 2011/0059157 A1 | 3/2011 | Awasthi et al. | |
| 2012/0264669 A1 | 10/2012 | Cristobal et al. | |
| 2016/0168408 A1 * | 6/2016 | Cho ......................... | C07C 57/13 |
| | | | 252/519.3 |

FOREIGN PATENT DOCUMENTS

| | | | | |
|---|---|---|---|---|
| CN | 102782112 A | | 11/2012 | |
| CN | 103623740 A * | | 3/2014 | ........... C07C 309/58 |
| DE | 43 40 042 A1 | | 6/1995 | |
| DE | 44 32 363 A1 | | 3/1996 | |
| JP | 28-001975 B2 | | 5/1953 | |
| JP | 63-142350 A | | 6/1988 | |
| JP | 11-140484 A | | 5/1999 | |
| JP | H11-140484 A * | | 5/1999 | ............... C11D 1/06 |
| JP | 2011-157354 A * | | 8/2011 | ........... C07C 69/675 |
| JP | 2011-157354 A | | 8/2011 | |
| JP | 2011-190184 A * | | 9/2011 | |
| JP | 2011-190184 A | | 9/2011 | |
| JP | 2013-129642 A | | 7/2013 | |
| WO | 2011/079459 A1 | | 7/2011 | |
| WO | 2012/061101 A1 | | 5/2012 | |

OTHER PUBLICATIONS

Buijnsters, P.J.J.A., et al., Cationic gemini surfactants based on tartaric acid: synthesis, aggregation, monollayer behaviour, and infraction with DNA, European Journal of Organic Chemistry, pp. 1397-1406 (Year: 2002).*
Evstigneeva, R. P., et al., Synthesis of ethyl alpha-(beta-carboxyethyl)-beta-methyllevulinate, Inst. Fine Chem. Technol., Moscow Zhurnal Obschchei Khimii, 31, pp. 441-441, 2 page abstract (Year: 1961).*
Shi, J. et al., The syntehsis and property of 2,3-bidodecylate butanedioic acid sodium, Huzxue Shiji, vol. 28, No. 8, pp. 483-484, (Year: 2006).*
CN 1036233740, Tang, S. et al., Gemini surfactant containing sulfonic group and sulfate group anions, and preparation method thereof, English translation 9 pages (Year: 2014).*
English translation of JP 28-001975 published May 8, 1953.

(Continued)

*Primary Examiner* — Yate' K Cutliff
(74) *Attorney, Agent, or Firm* — Sughrue Mion, PLLC

(57) ABSTRACT

The invention provides a novel hydrocarbon-containing carboxylic acid, hydrocarbon-containing sulfonic acid, hydrocarbon-containing sulfuric acid ester, or a salt thereof, and a surfactant. Each of them is a compound represented by the following formula (1):

$CR^1R^2R^4$—$CR^3R^5$—X-A wherein $R^1$ to $R^5$ are each H or a monovalent substituent; at least one of $R^1$ or $R^3$ is a group represented by the formula: —Y—$R^6$; at least one of $R^2$ or $R^5$ is a group represented by the formula: —X-A or a group represented by the formula: —Y—$R^6$; and As at the respective appearances are the same as or different from each other, and are each —COOM, —$SO_3$M, or —$OSO_3$M.

7 Claims, No Drawings

(56) References Cited

OTHER PUBLICATIONS

Germasheva, I. I. et al., "Influence of the structure of a hydrophobic radical on some colloidal and chemical properties of surfactants of the type of sulfosuccinates", Kolloidnyi Zhurnal, 1983, vol. 45, No. 3, pp. 546-549, p. 547 (13 pages total).
Shi, J. et al.. "The synthesis and property of 2,3-bidodecylate butanedioic acid sodium", Huaxue Shiji, 2006, vol. 28, No. 8, pp. 483-484, 506, pp. 483-484, 506 (13 pages total).
International Preliminary Report on Patentability dated Apr. 2, 2019 from the International Bureau in counterpart International Application No. PCT/JP2017/035372.
Acharya, D. P. et al., "Phase and Rheological Behavior of Novel Gemini-Type Surfactant Systems", The Journal of Physical Chemistry B, 2004, vol. 108, pp. 1790-1797, fig. 1.
Chau, H. N., et al., "Preparation of Dicarboxylic Acid-Type Gemini Surfactant via Diels-Alder Reaction & Ozone Oxidation", Journal of Oleo Science, 2013, vol. 62, No. 6, pp. 409-414, table 1.
Ono, Daisuke et al., "Preparation and Properties of Bis (sodium sulfate) Type of Cleavable Surfactants Derived from Diethyl Tartrate", Journal of Oleo Science, 2005, vol. 54, No. 1, pp. 51-57, Scheme 1.
Altenbach, H. et al., "Synthesis and Characterization of Novel Surfactants: Combination Products of Fatty Acids, Hydroxycarboxylic Acids", Journal of Surfactants and Detergents, 2010, vol. 13, pp. 399-407, fig. 2-3.
Pei, X. et al., "Wormlike Micelle Formation and Rheological Behavior in the Aqueous Solutions of Mixed Sulfate Gemini Surfactant without Spacer Group and Dodecyltrimethylammonium Bromide", Chinese Journal of Chemistry, 2011, vol. 29, pp. 2003-2006, Scheme 1.
Germasheva, I. I. et al., "Influence of the structure of a hydrophobic radical on some colloidal and chemical properties of surfactants of the type of sulfosuccinates", Kolloidnyi Zhurnal, 1983, vol. 45, No. 3, pp. 546-549, p. 547, ISSN: 0023-2912.
Shi, J. et al.. The synthesis and property of 2,3-bidodecylate butanedioic acid sodium, Huaxue Shiji, 2006, vol. 28, No. 8, pp. 483-484, 506, p. 483, ISSN: 0258-3283.
Wei, Wei et al., "Synthetic ultra-long chain fatty acyl based amphiphilic lipids as a dual function excipient for the production of surfactant-free solid lipid nanoparticles (SF-SLNs): a physicochemical study", Green Chemistry, Jun. 13, 2016, vol. 18, pp. 3962-3971, p. 3964.
Buijnsters, Petrus J. J. A., et al., "Cationic Gemini Surfactants Based on Tartaric Acid: Synthesis, Aggregation, Monolayer Behaviour, and Interaction with DNA", European Journal of Organic Chemistry, 2002, pp. 1397-1406, Scheme 1.
Buzby, George C., et al., "Rearrangement Accompanying the Permanganate Oxidation of Ethyl cis-2,2,4,4-Tetracarbetboxycyclobutane-I,3-dimalonate" Journal of Organic Chemistry, 1963, vol. 28, pp. 1082-1086, p. 1083, left column, ISSN: 0022-3263.
Registry(STN)(online], Apr. 17, 2009 [retrieved on Dec. 7, 2017] CAS reg. No. 1135685-31-2.
Registry(STN)[online], Apr. 17, 2009 [retrieved on Dec. 7, 2017] CAS reg. No. 1135684-39-7.
Registry (STN)[online], Apr. 16, 2009 (retrieved on Dec. 7, 2017] CAS reg. No. 1135422-78-4.
Registry (STN)[online], Apr. 16, 2009 (retrieved on Dec. 7, 2017] CAS reg. No. 1135361-73-7.
International Search Report of PCT/JP2017/035372 dated Dec. 19, 2017.
Communication dated Mar. 18, 2020 from European Patent Office in EP Application No. 17856399.5.
Eastoe et al., "Designed $CO_2$-Philes Stabilize Water-in-Carbon Dioxide Microemulsions", Angew. Chem. Int. Ed., vol. 45, 2006, pp. 3675-3677 (4 pages).

\* cited by examiner

HYDROCARBON-CONTAINING CARBOXYLIC ACID, HYDROCARBON-CONTAINING SULFONIC ACID, HYDROCARBON-CONTAINING SULFURIC ACID ESTER OR SALT THEREOF, AND SURFACTANT

CROSS REFERENCE TO RELATED APPLICATIONS

This application is a National Stage of International Application No. PCT/JP2017/035372 filed Sep. 29, 2017, claiming priority based on Japanese Patent Application Nos. 2016-195062 filed Sep. 30, 2016 and 2017-073087 filed Mar. 31, 2017.

TECHNICAL FIELD

The invention relates to hydrocarbon-containing carboxylic acids, hydrocarbon-containing sulfonic acids, hydrocarbon-containing sulfuric acid esters, or salts thereof, and surfactants.

BACKGROUND ART

Non-Patent Literature 1 discloses a gemini surfactant having the following structure.

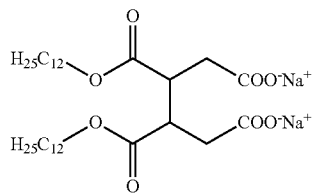

[Chem. 1]

CITATION LIST

Non-Patent Literature

Non-Patent Literature 1: Durga P. Acharya, and 3 other persons, "Phase and Rheological Behavior of Novel Gemini-Type Surfactant Systems", J. Phys. Chem. B, 2004, 108(5), pp. 1790-1797

SUMMARY OF INVENTION

Technical Problem

The invention aims to provide a novel hydrocarbon-containing carboxylic acid, hydrocarbon-containing sulfonic acid, hydrocarbon-containing sulfuric acid ester, or a salt thereof, and a surfactant.

Solution to Problem

The invention relates to a compound represented by the following formula (1):

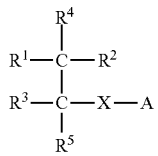

[Chem. 2]

wherein $R^1$ to $R^5$ are each H or a monovalent substituent; at least one of $R^1$ or $R^3$ is a group represented by the formula: —Y—$R^6$; and at least one of $R^2$ or $R^5$ is a group represented by the formula: —X-A or a group represented by the formula: —Y—$R^6$;

Xs at the respective appearances are the same as or different from each other, and are each a divalent linking group or a direct bond;

As at the respective appearances are the same as or different from each other, and are each —COOM, —$SO_3$M, or —$OSO_3$M, wherein M is H, a metal atom, $NR^7_4$, imidazolium optionally containing a substituent, pyridinium optionally containing a substituent, or phosphonium optionally containing a substituent, wherein $R^7$ is H or an organic group;

Ys at the respective appearances are the same as or different from each other, and are each a divalent linking group selected from the group consisting of —S(=O)$_2$—, —O—, —COO—, —OCO—, —$CONR^8$—, and —$NR^8$CO—, or a direct bond, wherein $R^8$ is H or an organic group;

$R^6$s at the respective appearances are the same as or different from each other, and are each an alkyl group containing two or more carbon atoms and optionally containing, between carbon atoms, at least one selected from the group consisting of a carbonyl group, an ester group, an amide group, and a sulfonyl group;

any two of $R^1$ to $R^5$ optionally bind to each other to form a ring;

with $R^6$ containing none of a carbonyl group, an ester group, an amide group, and a sulfonyl group, X is a divalent linking group containing at least one selected from the group consisting of a carbonyl group, an ester group, an amide group, and a sulfonyl group.

The compound is preferably a compound represented by the following formula (1-1) or a compound represented by the following formula (1-2).

The formula (1-1) is as follows:

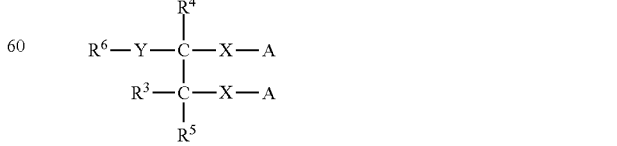

[Chem. 3]

wherein $R^3$ to $R^6$, X, A, and Y are defined as mentioned above.

The formula (1-2) is as follows:

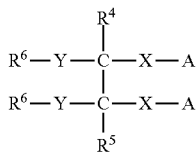

wherein $R^4$ to $R^6$, X, A, and Y are defined as mentioned above.

$R^4$ and $R^5$ are each preferably H or a C1-C4 alkyl group.

M is preferably H, Na, K, Li, or $NH_4$.

M is preferably Na, K, or $NH_4$.

M is preferably $NH_4$.

The invention also relates to a surfactant containing the above compound.

The invention also relates to an aqueous dispersant containing the above compound.

Advantageous Effects of Invention

The compound of the invention is a compound exhibiting a surfactant effect, and can suitably be used for anionic surfactants and aqueous dispersants.

DESCRIPTION OF EMBODIMENTS

The invention will be specifically described hereinbelow.

The term "organic group" as used herein means a group containing one or more carbon atoms or a group obtainable by removing one hydrogen atom from an organic compound, unless otherwise mentioned.

Examples of the "organic group" include:
an alkyl group optionally containing one or more substituents,
an alkenyl group optionally containing one or more substituents,
an alkynyl group optionally containing one or more substituents,
a cycloalkyl group optionally containing one or more substituents,
a cycloalkenyl group optionally containing one or more substituents,
a cycloalkadienyl group optionally containing one or more substituents,
an aryl group optionally containing one or more substituents,
an aralkyl group optionally containing one or more substituents,
a non-aromatic heterocyclic group optionally containing one or more substituents,
a heteroaryl group optionally containing one or more substituents,
a cyano group,
a formyl group,
RaO—,
RaCO—,
$RaSO_2$—,
RaCOO—,
RaNRaCO—,
RaCONRa—,
$RaSO_2NRa$—,
$RaNRaSO_2$—,
RaOCO—, and
$RaOSO_2$—,
wherein each Ra is independently
an alkyl group optionally containing one or more substituents,
an alkenyl group optionally containing one or more substituents,
an alkynyl group optionally containing one or more substituents,
a cycloalkyl group optionally containing one or more substituents,
a cycloalkenyl group optionally containing one or more substituents,
a cycloalkadienyl group optionally containing one or more substituents,
an aryl group optionally containing one or more substituents,
an aralkyl group optionally containing one or more substituents,
a non-aromatic heterocyclic group optionally containing one or more substituents, or
a heteroaryl group optionally containing one or more substituents.

The organic group is preferably an alkyl group optionally containing one or more substituents.

The term "substituent" as used herein means a group which can replace another atom or a group, unless otherwise mentioned. Examples of the "substituent" include an aliphatic group, an aromatic group, a heterocyclic group, an acyl group, an acyloxy group, an acylamino group, an aliphatic oxy group, an aromatic oxy group, a heterocyclic oxy group, an aliphatic oxycarbonyl group, an aromatic oxycarbonyl group, a heterocyclic oxycarbonyl group, a carbamoyl group, an aliphatic sulfonyl group, an aromatic sulfonyl group, a heterocyclic sulfonyl group, an aliphatic sulfonyloxy group, an aromatic sulfonyloxy group, a heterocyclic sulfonyloxy group, a sulfamoyl group, an aliphatic sulfonamide group, an aromatic sulfonamide group, a heterocyclic sulfonamide group, an amino group, an aliphatic amino group, an aromatic amino group, a heterocyclic amino group, an aliphatic oxycarbonylamino group, an aromatic oxycarbonylamino group, a heterocyclic oxycarbonylamino group, an aliphatic sulfinyl group, an aromatic sulfinyl group, an aliphatic thio group, an aromatic thio group, a hydroxy group, a cyano group, a sulfo group, a carboxy group, an aliphatic oxyamino group, an aromatic oxyamino group, a carbamoylamino group, a sulfamoyl amino group, a halogen atom, a sulfamoyl carbamoyl group, a carbamoyl sulfamoyl group, a dialiphatic oxyphosphinyl group, and a diaromatic oxyphosphinyl group.

The aliphatic group may be either saturated or unsaturated, and may contain any of a hydroxy group, an aliphatic oxy group, a carbamoyl group, an aliphatic oxycarbonyl group, an aliphatic thio group, an amino group, an aliphatic amino group, an acylamino group, a carbamoylamino group, and the like. Examples of the aliphatic group include alkyl groups containing one to eight, preferably one to four carbon atoms in total, such as a methyl group, an ethyl group, a vinyl group, a cyclohexyl group, and a carbamoylmethyl group.

The aromatic group may contain any of a nitro group, a halogen atom, an aliphatic oxy group, a carbamoyl group, an aliphatic oxycarbonyl group, an aliphatic thio group, an amino group, an aliphatic amino group, an acylamino group, a carbamoylamino group, and the like. Examples of the aromatic group include aryl groups containing six to twelve, preferably six to ten carbon atoms in total, such as a phenyl group, a 4-nitrophenyl group, a 4-acetylaminophenyl group, and a 4-methanesulfonylphenyl group.

The heterocyclic group may contain any of a halogen atom, a hydroxy group, an aliphatic oxy group, a carbamoyl group, an aliphatic oxycarbonyl group, an aliphatic thio group, an amino group, an aliphatic amino group, an acylamino group, a carbamoylamino group, and the like. Examples of the heterocyclic group include 5- or 6-membered heterocyclic groups containing two to twelve, preferably two to ten carbon atoms in total, such as a 2-tetrahydrofuryl group and a 2-pyrimidyl group.

The acyl group may contain any of an aliphatic carbonyl group, an arylcarbonyl group, a heterocyclic carbonyl group, a hydroxy group, a halogen atom, an aromatic group, an aliphatic oxy group, a carbamoyl group, an aliphatic oxycarbonyl group, an aliphatic thio group, an amino group, an aliphatic amino group, an acylamino group, a carbamoylamino group, and the like. Examples of the acyl group include acyl groups containing two to eight, preferably two to four carbon atoms in total, such as an acetyl group, a propanoyl group, a benzoyl group, and a 3-pyridinecarbonyl group.

The acylamino group may contain any of an aliphatic group, an aromatic group, a heterocyclic group, and the like, and may contain any of an acetylamino group, a benzoylamino group, a 2-pyridinecarbonylamino group, a propanoylamino group, and the like, for example. Examples of the acylamino group include acylamino groups containing two to twelve, preferably two to eight carbon atoms in total, and alkylcarbonylamino groups containing two to eight carbon atoms in total, such as an acetylamino group, a benzoylamino group, a 2-pyridinecarbonylamino group, and a propanoylamino group.

The aliphatic oxycarbonyl group may be either saturated or unsaturated, and may contain any of a hydroxy group, an aliphatic oxy group, a carbamoyl group, an aliphatic oxycarbonyl group, an aliphatic thio group, an amino group, an aliphatic amino group, an acylamino group, a carbamoylamino group, and the like. Examples of the aliphatic oxycarbonyl group include alkoxycarbonyl groups containing two to eight, preferably two to four carbon atoms in total, such as a methoxycarbonyl group, an ethoxycarbonyl group, and a (t)-butoxycarbonyl group.

The carbamoyl group may contain any of an aliphatic group, an aromatic group, a heterocyclic group, and the like. Examples of the carbamoyl group include an unsubstituted carbamoyl group and alkylcarbamoyl groups containing two to nine carbon atoms in total, preferably an unsubstituted carbamoyl group and alkylcarbamoyl groups containing two to five carbon atoms in total, such as a N-methylcarbamoyl group, a N,N-dimethylcarbamoyl group, and a N-phenylcarbamoyl group.

The aliphatic sulfonyl group may be either saturated or unsaturated, and may contain any of a hydroxy group, an aromatic group, an aliphatic oxy group, a carbamoyl group, an aliphatic oxycarbonyl group, an aliphatic thio group, an amino group, an aliphatic amino group, an acylamino group, a carbamoylamino group, and the like. Examples of the aliphatic sulfonyl group include alkyl sulfonyl groups containing one to six, preferably one to four carbon atoms in total, such as a methanesulfonyl group.

The aromatic sulfonyl group may contain any of a hydroxy group, an aliphatic group, an aliphatic oxy group, a carbamoyl group, an aliphatic oxycarbonyl group, an aliphatic thio group, an amino group, an aliphatic amino group, an acylamino group, a carbamoylamino group, and the like. Examples of the aromatic sulfonyl group include arylsulfonyl groups containing six to ten carbon atoms in total, such as a benzenesulfonyl group.

The amino group may contain any of an aliphatic group, an aromatic group, a heterocyclic group, and the like.

The acylamino group may contain any of an acetylamino group, a benzoylamino group, a 2-pyridinecarbonylamino group, a propanoylamino group, and the like. Examples of the acylamino group include acylamino groups containing two to twelve, preferably two to eight carbon atoms in total, more preferably alkylcarbonylamino groups containing two to eight carbon atoms in total, such as an acetylamino group, a benzoylamino group, a 2-pyridinecarbonylamino group, and a propanoylamino group.

The aliphatic sulfonamide group, the aromatic sulfonamide group, and the heterocyclic sulfonamide group may respectively be a methanesulfonamide group, a benzene sulfonamide group, and a 2-pyridinesulfonamide group, for example.

The sulfamoyl group may contain any of an aliphatic group, an aromatic group, a heterocyclic group, and the like. Examples of the sulfamoyl group include a sulfamoyl group, alkylsulfamoyl groups containing one to nine carbon atoms in total, dialkylsulfamoyl groups containing two to ten carbon atoms in total, arylsulfamoyl groups containing seven to thirteen carbon atoms in total, and heterocyclic sulfamoyl groups containing two to twelve carbon atoms in total, more preferably a sulfamoyl group, alkylsulfamoyl groups containing one to seven carbon atoms in total, dialkylsulfamoyl groups containing three to six carbon atoms in total, arylsulfamoyl groups containing six to eleven carbon atoms in total, and heterocyclic sulfamoyl groups containing two to ten carbon atoms in total, such as a sulfamoyl group, a methylsulfamoyl group, a N,N-dimethylsulfamoyl group, a phenylsulfamoyl group, and a 4-pyridinesulfamoyl group.

The aliphatic oxy group may be either saturated or unsaturated, and may contain any of a methoxy group, an ethoxy group, an i-propyloxy group, a cyclohexyloxy group, a methoxyethoxy group, and the like. Examples of the aliphatic oxy group include alkoxy groups containing one to eight, preferably one to six carbon atoms in total, such as a methoxy group, an ethoxy group, an i-propyloxy group, a cyclohexyloxy group, and a methoxyethoxy group.

The aromatic amino group and the heterocyclic amino group each may contain any of an aliphatic group, an aliphatic oxy group, a halogen atom, a carbamoyl group, a heterocyclic group ring-fused with the aryl group, and an aliphatic oxycarbonyl group, preferably any of an aliphatic group containing one to four carbon atoms in total, an aliphatic oxy group containing one to four carbon atoms in total, a halogen atom, a carbamoyl group containing one to four carbon atoms in total, a nitro group, and an aliphatic oxycarbonyl group containing two to four carbon atoms in total.

The aliphatic thio group may be either saturated or unsaturated, and examples thereof include alkylthio groups containing one to eight, more preferably one to six carbon atoms in total, such as a methylthio group, an ethylthio group, a carbamoylmethylthio group, and a t-butylthio group.

The carbamoylamino group may contain any of an aliphatic group, an aryl group, a heterocyclic group, and the like. Examples of the carbamoylamino group include a carbamoylamino group, alkylcarbamoylamino groups containing two to nine carbon atoms in total, dialkylcarbamoylamino groups containing three to ten carbon atoms in total, arylcarbamoylamino groups containing seven to thirteen carbon atoms in total, and heterocyclic carbamoylamino groups containing three to twelve carbon atoms in total, preferably a carbamoylamino group, alkylcarbamoylamino groups containing two to seven carbon atoms in total, dialkylcarbamoylamino groups containing three to six carbon atoms in total, arylcarbamoylamino groups containing seven to eleven carbon atoms in total, and heterocyclic carbamoylamino group containing three to ten carbon atoms in total, such as a carbamoylamino group, a methylcarbamoylamino group, a N,N-dimethylcarbamoylamino group, a phenylcarbamoylamino group, and a 4-pyridinecarbamoylamino group.

The compound of the invention is represented by the following formula (1):

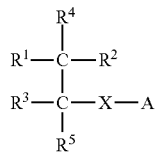

[Chem. 5]

wherein $R^1$ to $R^5$ are each H or a monovalent substituent; at least one of $R^1$ or $R^3$ is a group represented by the formula: —Y—$R^6$; at least one of $R^2$ or $R^5$ is a group represented by the formula: —X-A or a group represented by the formula: —Y—$R^6$; and any two of $R^1$ to $R^5$ optionally bind to each other to form a ring.

The substituent which may be contained in the alkyl group for $R^1$ is preferably a halogen atom, a C1-C10 linear or branched alkyl group, a C3-C10 cyclic alkyl group, or a hydroxy group, particularly preferably a methyl group or an ethyl group.

The alkyl group for $R^1$ preferably contains no carbonyl group.

In the alkyl group, 75% or less of the hydrogen atoms binding to any carbon atom may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

$R^1$ is preferably a C1-C10 linear or branched alkyl group optionally containing a substituent or a C3-C10 cyclic alkyl group optionally containing a substituent, more preferably a C1-C10 linear or branched alkyl group containing no carbonyl group or a C3-C10 cyclic alkyl group containing no carbonyl group, still more preferably a C1-C10 linear or branched alkyl group containing no substituent, further more preferably a C1-C3 linear or branched alkyl group containing no substituent, particularly preferably a methyl group (—$CH_3$) or an ethyl group (—$C_2H_5$), most preferably a methyl group (—$CH_3$).

The monovalent substituent is preferably a group represented by the formula: —Y—$R^6$, a group represented by the formula: —X-A, —H, a C1-C20 alkyl group optionally containing a substituent, —$NH_2$, —$NHR^9$ (wherein $R^9$ is an organic group), —OH, —$COOR^9$ (wherein $R^9$ is an organic group), or —$OR^9$ (wherein $R^9$ is an organic group). The alkyl group preferably contains 1 to 10 carbon atoms.

$R^9$ is preferably a C1-C10 alkyl group or a C1-C10 alkylcarbonyl group, more preferably a C1-C4 alkyl group or a C1-C4 alkylcarbonyl group.

In the formula, Xs at the respective appearances are the same as or different from each other, and are each a divalent linking group or a direct bond.

With $R^6$ containing none of a carbonyl group, an ester group, an amide group, and a sulfonyl group, X is a divalent linking group containing at least one selected from the group consisting of a carbonyl group, an ester group, an amide group, and a sulfonyl group.

X is preferably a divalent linking group containing at least one bond selected from the group consisting of —CO—, —S(=O)$_2$—, —O—, —COO—, —OCO—, —S(=O)$_2$—O—, —O—S(=O)$_2$—, —CONR$^8$—, and —NR$^8$CO—, a C1-C10 alkylene group, or a direct bond. $R^8$ is H or an organic group.

$R^8$ is preferably H or a C1-C10 organic group, more preferably H or a C1-C4 organic group, still more preferably H.

In the formula, As at the respective appearances are the same as or different from each other, and are each —COOM, —SO$_3$M, or —OSO$_3$M, wherein M is H, a metal atom, NR$^7_4$, imidazolium optionally containing a substituent, pyridinium optionally containing a substituent, or phosphonium optionally containing a substituent, wherein $R^7$ is H or an organic group, and the four $R^7$s are the same as or different from each other.

$R^7$ is preferably H or a C1-C10 organic group, more preferably H or a C1-C4 organic group.

Examples of the metal atom include alkali metals (Group 1) and alkaline earth metals (Group 2), and Na, K, or Li is preferred.

M is preferably H, a metal atom, or NR$^7_4$, more preferably H, an alkali metal (Group 1), an alkaline earth metal (Group 2), or NR$^7_4$, still more preferably H, Na, K, Li, or NH$_4$, further more preferably Na, K, or NH$_4$, particularly preferably Na or NH$_4$, most preferably NH$_4$.

In the formula, Ys at the respective appearances are the same as or different from each other, and are each a divalent linking group selected from the group consisting of —S(=O)$_2$—, —O—, —COO—, —OCO—, —CONR$^8$—, and —NR$^8$CO—, or a direct bond, wherein $R^8$ is H or an organic group.

Y is preferably a divalent linking group selected from the group consisting of a direct bond, —O—, —COO—, —OCO—, —CONR$^8$—, and —NR$^8$CO—, more preferably a divalent linking group selected from the group consisting of a direct bond, —COO—, and —OCO—.

$R^8$ is preferably H or a C1-C10 organic group, more preferably H or a C1-C4 organic group, still more preferably H.

In the formula, $R^6$s at the respective appearances are the same as or different from each other, and are each an alkyl group containing two or more carbon atoms and optionally containing, between carbon atoms, at least one selected from the group consisting of a carbonyl group, an ester group, an amide group, and a sulfonyl group. The organic group for $R^6$ preferably contains 2 to 20, more preferably 2 to 10 carbon atoms.

The alkyl group for $R^6$ may contain, between carbon atoms, one or two or more of at least one group selected from the group consisting of a carbonyl group, an ester group, an amide group, and a sulfonyl group, but the alkyl group contains no such groups at ends. In the alkyl group for $R^6$, 75% or less of the hydrogen atoms binding to any carbon atom may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

$R^6$ is preferably
a group represented by the formula: $-R^{10}-CO-R^{11}$,
a group represented by the formula: $-R^{10}-COO-R^{11}$,
a group represented by the formula: $-R^{11}$,
a group represented by the formula: $-R^{10}-NR^8CO-R^{11}$, or
a group represented by the formula: $-R^{10}-CONR^8-R^{11}$,
wherein $R^8$ is H or an organic group; $R^{10}$ is an alkylene group; and $R^{11}$ is an alkyl group optionally containing a substituent.

$R^6$ is more preferably a group represented by the formula: $-R^{10}-CO-R^{11}$.

$R^8$ is preferably H or a C1-C10 organic group, more preferably H or a C1-C4 organic group, still more preferably H.

The alkylene group for $R^{10}$ preferably contains one or more, more preferably 3 or more carbon atoms, whereas it preferably contains 20 or less, more preferably 12 or less, still more preferably 10 or less, particularly preferably 8 or less carbon atoms. The alkylene group for $R^{10}$ preferably contains 1 to 20, more preferably 1 to 10, still more preferably 3 to 10 carbon atoms.

The alkyl group for $R^{11}$ may contain 1 to 20 carbon atoms. The number of the carbon atoms is preferably 1 to 15, more preferably 1 to 12, still more preferably 1 to 10, further more preferably 1 to 8, still further more preferably 1 to 6, still much more preferably 1 to 3, particularly preferably 1 or 2, most preferably 1. The alkyl group for $R^{11}$ preferably consists only of any of primary carbons, secondary carbons, and tertiary carbons, particularly preferably consists only of primary carbons and secondary carbons. In other words, $R^1$ is preferably a methyl group, an ethyl group, a n-propyl group, or an isopropyl group, most preferably a methyl group.

The compound of the invention is preferably a compound represented by the following formula (1-1), a compound represented by the following formula (1-2), or a compound represented by the following formula (1-3), more preferably a compound represented by the formula (1-1) or a compound represented by the formula (1-2).

The formula (1-1) is as follows:

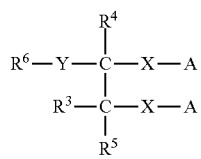

[Chem. 6]

wherein $R^3$ to $R^6$, X, A, and Y are defined as mentioned above.

The formula (1-2) is as follows:

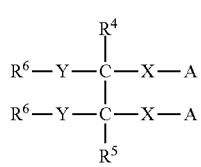

[Chem. 7]

wherein $R^4$ to $R^6$, X, A, and Y are defined as mentioned above.

The formula (1-3) is as follows:

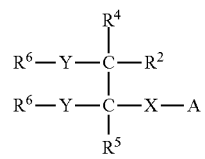

[Chem. 8]

wherein $R^2$, $R^4$ to $R^6$, X, A, and Y are defined as mentioned above.

The group represented by the formula: $-X-A$ is preferably
—COOM,
—$R^{12}$COOM,
—$SO_3M$,
—$OSO_3M$,
—$R^{12}SO_3M$,
—$R^{12}OSO_3M$,
—OCO—$R^{12}$—COOM,
—OCO—$R^{12}$—$SO_3M$,
—OCO—$R^{12}$—$OSO_3M$,
—COO—$R^{12}$—COOM,
—COO—$R^{12}$—$SO_3M$,
—COO—$R^{12}$—$OSO_3M$,
—$CONR^8$—$R^{12}$—COOM,
—$CONR^8$—$R^{12}$—$SO_3M$,
—$CONR^8$—$R^{12}$—$OSO_3M$,
—$NR^8CO$—$R^{12}$—COOM,
—$NR^8CO$—$R^{12}$—$SO_3M$,
—$NR^8CO$—$R^{12}$—$OSO_3M$,
—$OS(=O)_2$—$R^{12}$—COOM,
—$OS(=O)_2$—$R^{12}$—$SO_3M$, or
—$OS(=O)_2$—$R^{12}$—$OSO_3M$,
wherein $R^8$ and M are defined as mentioned above; and $R^{12}$ is a C1-C10 alkylene group.

In the alkylene group for $R^{12}$, 75% or less of the hydrogen atoms binding to any carbon atom may be replaced by halogen atoms, 50% or less thereof may be replaced by halogen atoms, or 25% or less thereof may be replaced by halogen atoms. The alkylene group is preferably a non-halogenated alkylene group containing no halogen atoms such as fluorine atoms and chlorine atoms.

The group represented by the formula: $-Y-R^6$ is preferably
a group represented by the formula: $-R^{10}-CO-R^{11}$,
a group represented by the formula: $-OCO-R^{10}-CO-R^{11}$,
a group represented by the formula: $-COO-R^{10}-CO-R^{11}$,
a group represented by the formula: $-OCO-R^{10}-COO-R^{11}$,
a group represented by the formula: $-COO-R^{11}$,
a group represented by the formula: $-NR^8CO-R^{10}-CO-R^{11}$, or
a group represented by the formula: $-CONR^8-R^{10}-NR^8CO-R^{11}$,
wherein $R^8$, $R^{10}$, and $R^{11}$ are defined as mentioned above.

In the formula, $R^4$ and $R^5$ are each individually preferably H or a C1-C4 alkyl group.

In the alkyl groups for $R^4$ and $R^5$, 75% or less of the hydrogen atoms binding to any carbon atom may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

$R^3$ in the formula (1-1) is preferably H or a C1-C20 alkyl group optionally containing a substituent, more preferably H or a C1-C20 alkyl group containing no substituent, still more preferably H.

In the alkyl group for $R^3$, 75% or less of the hydrogen atoms binding to any carbon atom may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

$R^2$ in the formula (1-3) is preferably H, OH, or a C1-C20 alkyl group optionally containing a substituent, more preferably H, OH, or a C1-C20 alkyl group containing no substituent, still more preferably H or OH.

In the alkyl group for $R^2$, 75% or less of the hydrogen atoms binding to any carbon atom may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The compound of the invention may suitably be produced by a production method including:

a step (11) of reacting a carboxylic acid represented by the formula: $R^6$—COOH (wherein $R^6$ is defined as mentioned above) and a halogenating agent to provide a carboxylic acid halide represented by the formula: $R^6$—COZ (wherein $R^6$ is defined as mentioned above; and Z is a halogen atom); and a step (12) of reacting the carboxylic acid halide and a compound re sented by the following formula:

[Chem. 9]

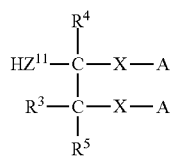

(wherein $R^3$ to $R^5$, X, and A are defined as mentioned above; $Z^{11}$ is —CH$_2$O—, —O—, or —NH—) to form a compound (12) represented by the following formula:

[Chem. 10]

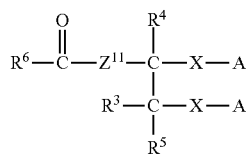

wherein $R^3$ to $R^6$, X, A, and $Z^{11}$ are defined as mentioned above.

$R^3$ in the formula for the above acid compound is preferably a group represented by the formula: —$Z^{11}$H (wherein $Z^{11}$ is defined as mentioned above) or —H. With $R^3$ which is a group represented by the formula: —$Z^{11}$H, this group reacts with the carboxylic acid halide in the step (12) to generate a group represented by the formula: —$Z^{11}$—CO—$R^6$, wherein $R^6$ and $Z^{11}$ are defined as mentioned above.

Examples of the halogenating agent used in the step (11) include oxalyl chloride, thionyl chloride, diethylaminosulfur trifluoride (DAST), Deoxo-Fluor, and 1,1,2,2-tetrafluoro-N,N-dimethylethylamine (TFEDMA).

Z is preferably F or Cl, more preferably Cl.

For the reaction ratio between the carboxylic acid and the halogenating agent in the step (11), the amount of the halogenating agent is preferably 0.6 to 5.0 mol, more preferably 0.8 to 2.0 mol, relative to 1 mol of the carboxylic acid, so as to improve the yield and to reduce the waste. The amount of the halogenating agent is also preferably 0.5 to 10 mol, more preferably 0.6 to 5.0 mol.

The reaction in the step (11) may be performed in a solvent. Examples of the solvent include esters, ketones, aromatic hydrocarbons, ethers, nitrogen-containing polar organic compounds, halogenated hydrocarbons, nitriles, pyridines, and mixtures thereof.

Examples of the esters include ethyl acetate, butyl acetate, ethylene glycol monomethyl ether acetate, and propylene glycol monomethyl ether acetate (PGMEA, also known as 1-methoxy-2-acetoxypropane). Ethyl acetate is preferred.

Examples of the ketones include acetone, methyl ethyl ketone, methyl isobutyl ketone, cyclohexanone, and diacetone alcohol. Acetone is preferred.

Examples of the aromatic hydrocarbons include benzene, toluene, and xylene. Benzene and toluene are preferred.

Examples of the ethers include diethyl ether, tetrahydrofuran, dioxane, and diethylene glycol diethyl ether. Diethyl ether and tetrahydrofuran are preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the halogenated hydrocarbons include dichloromethane, dichiorcethane, chloroform, chlorobenzene, and o-dichlorobenzene. Dichloromethane and chloroform are preferred.

Examples of the nitriles include acetonitrile, propionitrile, butyronitrile, isobutyronitrile, and benzonitrile. Acetonitrile is preferred.

The reaction temperature in the step (11) is preferably 0° C. to 150° C., more preferably 20° C. to 100° C. The reaction temperature is also preferably −78° C. to 150° C., more preferably 0° C. to 100° C.

The reaction pressure in the step (11) is preferably 0 to 5 MPa, more preferably 0.1 to 1.0 MPa.

The reaction duration in the step (11) is preferably 0.1 to 72 hours, more preferably 0.1 to 48 hours.

For the reaction ratio between the carboxylic acid halide and the acid compound in the step (12), the amount of the acid compound is preferably 0.5 to 10 mol, more preferably 0.6 to 5.0 mol, still more preferably 0.8 to 2.0 mol, relative to 1 mol of the carboxylic acid halide, so as to improve the yield and to reduce the waste.

The reaction in the step (12) is preferably performed in the presence of an acid. Examples of the acid include sulfuric acid, methanesulfonic acid, and p-toluenesulfonic acid. Sulfuric acid is preferred.

In order to improve the yield and to reduce the waste, the amount of the acid used in the step (12) is preferably 0.00001 to 1.0 mol, more preferably 0.0001 to 1.0 mol, still more preferably 0.00005 to 0.1 mol, particularly preferably 0.001 to 0.1 mol, relative to 1 mol of the carboxylic acid halide.

The reaction temperature in the step (12) is preferably 0° C. to 150° C., more preferably 20° C. to 100° C.

The reaction pressure in the step (12) is preferably 0 to 5 MPa, more preferably 0.1 to 1.0 MPa.

The reaction duration in the step (12) is preferably 0.1 to 72 hours, more preferably 0.1 to 48 hours.

The compound of the invention may also suitably be produced by a production method including a step (21) of reacting a compound (20) represented by the following formula:

[Chem. 11]

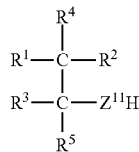

(wherein $R^1$ to $R^5$ are defined as mentioned above; and $Z^{11}$ is —$CH_2O$—, —O—, or —NH—) and an acid anhydride represented by the following formula:

[Chem. 12]

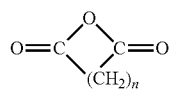

(wherein n is an integer of 1 to 5) to provide a compound (21) represented by the following formula:

[Chem. 13]

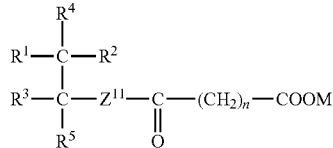

wherein $R^1$ to $R^5$, $Z^{11}$, M, and n are defined as mentioned above.

$R^2$ in the formula of the compound (20) is preferably a group represented by the formula: —$Z^{11}$H (wherein $Z^{11}$ is defined as mentioned above) or —H. With $R^2$ which is a group represented by the formula: —$Z^{11}$H, this group reacts with the acid anhydride in the step (21) to generate a group represented by the formula: —$Z^{11}$—CO—$(CH_2)_n$—COOM, wherein $Z^{11}$, M, and n are defined as mentioned above. The compound (20) may be a hydrochloric acid salt or a sulfuric acid salt as long as it has the structure represented by the above formula.

For the reaction ratio between the compound (20) and the acid anhydride in the step (21), the amount of the acid anhydride is preferably 0.5 to 10 mol, more preferably 0.6 to 5.0 mol, still more preferably 1.2 to 10 mol, particularly preferably 1.6 to 4.0 mol, relative to 1 mol of the compound (20), so as to improve the yield and to reduce the waste.

The reaction in the step (21) may be performed in the presence of a base.

Examples of the base include amines, potassium hydroxide, sodium hydroxide, and potassium carbonate.

Examples of the amines include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Pyridine or triethylamine is preferred.

The reaction temperature in the step (21) is preferably 0° C. to 150° C., more preferably 20° C. to 80° C. The reaction temperature is also preferably −78° C. to 150° C., more preferably 0° C. to 100° C.

The reaction pressure in the step (21) is preferably 0 to 5 MPa, more preferably 0.1 to 1 MPa.

The reaction duration in the step (21) is preferably 0.1 to 72 hours, more preferably 0.1 to 48 hours.

The compound of the invention may also suitably be produced by a production method including:

a step (31) of reacting a tartaric acid ester represented by the following formula:

[Chem. 14]

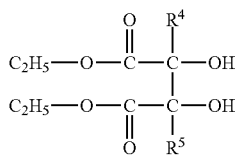

(wherein $R^4$ and $R^5$ are defined as mentioned above) and an amine represented by the formula: $R^6R^8$—NH (wherein $R^6$ and $R^8$ are defined as mentioned above) to provide a compound (31) represented by the following formula:

[Chem. 15]

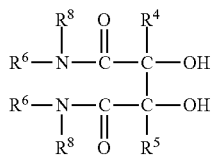

(wherein $R^4$ to $R^6$ and $R^8$ are defined as mentioned above); and a step (32) of reacting the compound (31) and a chlorosulfonic acid represented by the following formula:

[Chem. 16]

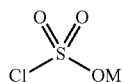

(wherein M is defined as mentioned above) to provide a compound (32) represented by the following formula:

[Chem. 17]

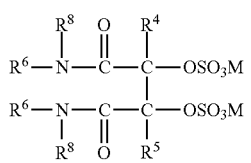

wherein $R^4$ to $R^6$, $R^8$, and M are defined as mentioned above.

For the reaction ratio between the tartaric acid ester and the amine in the step (31), the amount of the amine is preferably 0.5 to 10 mol, more preferably 0.6 to 5.0 mol, still more preferably 1.2 to 5 mol, particularly preferably 1.6 to 5.0 mol, relative to 1 mol of the tartaric acid ester, so as to improve the yield and to reduce the waste.

The reaction in the step (31) may be performed in a solvent. The solvent is preferably an organic solvent, still more preferably an alcohol, an ether, a halogenated hydrocarbon, a nitrogen-containing polar organic compound, or a nitrile.

Examples of the alcohol include methanol, ethanol, 1-propanol, and isopropanol.

Examples of the ether include tetrahydrofuran, dioxane, and diethylene glycol diethyl ether.

Examples of the halogenated hydrocarbon include dichloromethane, dichloroethane, chloroform, chlorobenzene, and o-dichlorobenzene.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the nitrile include acetonitrile, propionitrile, butyronitrile, isobutyronitrile, and benzonitrile.

The reaction temperature in the step (31) is preferably 0° C. to 150° C., more preferably 20° C. to 100° C.

The reaction pressure in the step (31) is preferably 0 to 5 MPa, more preferably 0.1 to 1 MPa.

The reaction duration in the step (31) is preferably 0.1 to 72 hours, more preferably 0.1 to 48 hours.

For the reaction ratio between the compound (31) and the chlorosulfonic acid in the step (32), the amount of the chlorosulfonic acid is preferably 1.0 to 50 mol, more preferably 1.6 to 20 mol, relative to 1 mol of the compound (31), so as to improve the yield and to reduce the waste.

The reaction in the step (32) is preferably performed in the presence of a base. Examples of the base include alkali metal hydroxides, alkaline earth metal hydroxides, and amines. Amines are preferred.

Examples of the amines in the step (32) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Triethylamine is preferred.

In order to improve the yield and to reduce the waste, the amount of the base used in the step (32) is preferably 0.1 to 50 mol, more preferably 1.0 to 20 mol, relative to 1 mol of the compound (31).

The reaction in the step (32) may be performed in a solvent. The solvent is preferably an organic solvent, more preferably an aprotic polar solvent, still more preferably a nitrile, a halogenated hydrocarbon, dimethyl sulfoxide, sulfolane, a nitrogen-containing polar organic compound, or an ether.

Examples of the nitrile include acetonitrile, propionitrile, butyronitrile, isobutyronitrile, and benzonitrile. Acetonitrile is preferred.

Examples of the halogenated hydrocarbon include dichloromethane, dichloroethane, chloroform, chlorobenzene, and o-dichlorobenzene. Dichloromethane and chloroform are preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the ether include diethyl ether, tetrahydrofuran, dioxane, and diethylene glycol diethyl ether. Diethyl ether is preferred.

The reaction temperature in the step (32) is preferably −78° C. to 150° C., more preferably −78° C. to 100° C., still more preferably −20° C. to 100° C., particularly preferably 10° C. to 50° C.

The reaction pressure in the step (32) is preferably 0 to 5 MPa, more preferably 0.1 to 1.0 Pa.

The reaction duration in the step (32) is preferably 0.1 to 72 hours, more preferably 0.1 to 48 hours.

The compound of the invention may also suitably be produced by a production method including a step (41) of reacting an alcohol represented by the following formula:

[Chem. 18]

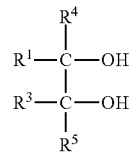

(wherein $R^1$ and $R^3$ to $R^5$ are defined as mentioned above) and an acid anhydride represented by the following formula:

[Chem. 19]

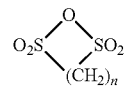

(wherein n is an integer of 1 to 5) to provide a compound (41) represented by the following formula:

[Chem. 20]

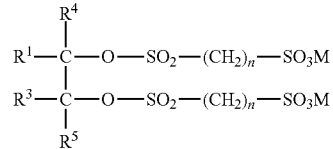

wherein $R^1$, $R^3$ to $R^5$, M, and n are defined as mentioned above.

For the reaction ratio between the alcohol and the acid anhydride in the step (41), the amount of the acid anhydride is preferably 0.5 to 10 mol, more preferably 0.6 to 4.0 mol, still more preferably 1.2 to 4.0 mol, particularly preferably 1.6 to 4.0 mol, relative to 1 mol of the alcohol, so as to improve the yield and to reduce the waste.

The reaction in the step (41) may be performed in the presence of a base.

Examples of the base include amines, potassium hydroxide, sodium hydroxide, and potassium carbonate.

Examples of the amines include tertiary amines such as trimethylamine, triethylamine, tributylamine, N,N-dimethylaniline, dimethylbenzylamine, and N,N,N',N'-tetramethyl- 1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Pyridine or triethylamine is preferred.

The reaction temperature in the step (41) is preferably −78° C. to 150° C., more preferably 0° C. to 150° C., still more preferably 0° C. to 100° C., particularly preferably 20° C. to 80° C.

The reaction pressure in the step (41) is preferably 0 to 5 MPa, more preferably 0.1 to 1 MPa.

The reaction duration in the step (41) is preferably 0.1 to 72 hours, more preferably 0.1 to 48 hours.

The compound of the invention may also suitably be produced by a production method including:

the step (31) of reacting a tartaric acid ester represented by the following formula:

[Chem. 21]

$$\begin{array}{c} \text{O} \quad R^4 \\ \| \quad | \\ C_2H_5-O-C-C-OH \\ | \\ C_2H_5-O-C-C-OH \\ \| \quad | \\ \text{O} \quad R^5 \end{array}$$

(wherein $R^4$ and $R^5$ are defined as mentioned above) and an amine represented by the formula: $R^6R^8$—NH (wherein $R^6$ and $R^8$ are defined as mentioned above) to provide a compound (31) represented by the following formula:

[Chem. 22]

$$\begin{array}{c} R^8 \quad \text{O} \quad R^4 \\ | \quad \| \quad | \\ R^6-N-C-C-OH \\ | \\ R^6-N-C-C-OH \\ | \quad \| \quad | \\ R^8 \quad \text{O} \quad R^5 \end{array}$$

(wherein $R^4$ to $R^6$ and $R^8$ are defined as mentioned above); and a step (51) of reacting the compound (31) and an acid anhydride represented by the following formula:

[Chem. 23]

$$O=C\underset{(CH_2)_n}{\overset{O}{\diagdown\diagup}}C=O,$$

(wherein n is an integer of 1 to 5) to provide a compound (51) represented by the following formula:

[Chem. 24]

$$\begin{array}{c} R^8 \quad \text{O} \quad R^4 \quad \quad \text{O} \\ | \quad \| \quad | \quad \quad \| \\ R^6-N-C-C-O-C-(CH_2)_n-COOM \\ | \\ R^6-N-C-C-O-C-(CH_2)_n-COOM \\ | \quad \| \quad | \quad \quad \| \\ R^8 \quad \text{O} \quad R^5 \quad \quad \text{O} \end{array}$$

wherein $R^4$ to $R^6$, $R^8$, M, and n are defined as mentioned above.

For the reaction ratio between the compound (31) and the acid anhydride in the step (51), the amount of the acid anhydride is preferably 0.5 to 10 mol, more preferably 0.6 to 4.0 mol, still more preferably 1.2 to 4.0 mol, particularly preferably 1.6 to 4.0 mol, relative to 1 mol of the compound (31), so as to improve the yield and to reduce the waste.

The reaction in the step (51) may be performed in the presence of a base.

Examples of the base include amines, potassium hydroxide, sodium hydroxide, and potassium carbonate.

Examples of the amines include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Pyridine or triethylamine is preferred.

The reaction temperature in the step (51) is preferably −78° C. to 150° C., more preferably 0° C. to 150° C., still more preferably 0° C. to 100° C., particularly preferably 20° C. to 80° C.

The reaction pressure in the step (51) is preferably 0 to 5 MPa, more preferably 0.1 to 1 MPa.

The reaction duration in the step (51) is preferably 0.1 to 72 hours, more preferably 0.1 to 48 hours.

The compound of the invention may also suitably be produced by a production method including:

a step (61) of reacting an alcohol represented by the formula: $R^6$—OH (wherein $R^6$ is defined as mentioned above) and a fumaric acid halide to provide a compound (61) represented by the following formula:

[Chem. 25]

$$\begin{array}{c} \text{O} \\ \| \\ R^6-O-C-CH \\ \| \\ R^6-O-C-CH \\ \| \\ \text{O} \end{array}$$

(wherein $R^6$ is defined as mentioned above); and a step (62) of reacting the compound (61) and a sulfonating agent such as sodium hydrogen sulfite to provide a compound (62) represented by the following formula:

[Chem. 26]

$$\begin{array}{c} \text{O} \\ \| \\ R^6-O-C-CH-OSO_3X \\ | \\ R^6-O-C-CH_2 \\ \| \\ \text{O} \end{array}$$

wherein $R^6$ and X are defined as mentioned above.

Examples of the fumaric acid halide used in the step (61) include fumaryl chloride, fumaryl fluoride, and fumaryl bromide.

For the reaction ratio between the alcohol and the fumaric acid halide in the step (61), the amount of the fumaric acid halide is preferably 0.1 to 10 mol, more preferably 0.1 to 2.0 mol, still more preferably 0.1 to 2.0 mol, particularly preferably 0.2 to 0.7 mol, relative to 1 mol of the alcohol, so as to improve the yield and to reduce the waste.

The reaction in the step (61) may be performed in a solvent. Examples of the solvent include esters, ketones, aromatic hydrocarbons, ethers, nitrogen-containing polar organic compounds, halogenated hydrocarbons, nitriles, pyridines, and mixtures thereof.

Examples of the esters include ethyl acetate, butyl acetate, ethylene glycol monomethyl ether acetate, and propylene glycol monomethyl ether acetate (PGMEA, also known as 1-methoxy-2-acetoxypropane). Ethyl acetate is preferred.

Examples of the ketones include acetone, methyl ethyl ketone, methyl isobutyl ketone, cyclohexanone, and diacetone alcohol. Acetone is preferred.

Examples of the aromatic hydrocarbons include benzene, toluene, and xylene. Benzene and toluene are preferred.

Examples of the ethers include diethyl ether, tetrahydrofuran, dioxane, and diethylene glycol diethyl ether. Diethyl ether and tetrahydrofuran are preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the halogenated hydrocarbons include dichloromethane, dichloroethane, chloroform, chlorobenzene, and o-dichlorobenzene. Dichloromethane and chloroform are preferred.

Examples of the nitriles include acetonitrile, propionitrile, butyronitrile, isobutyronitrile, and benzonitrile. Acetonitrile is preferred.

The reaction temperature in the step (61) is preferably −78° C. to 200° C., more preferably −20° C. to 150° C.

The reaction pressure in the step (61) is preferably 0 to 5.0 MPa, more preferably 0.1 to 1.0 MPa.

The reaction duration in the step (61) is preferably 0.1 to 72 hours, more preferably 0.1 to 48 hours.

In the step (62), the compound (61) containing a double bond and a sulfonating agent such as sodium hydrogen sulfite cause an addition reaction, and thereby the compound (62) is generated.

For the reaction ratio between the compound (61) and the sulfonating agent in the step (62), the amount of the sulfonating agent is preferably 0.5 to 20.0 mol, more preferably 0.6 to 10.0 mol, still more preferably 0.8 to 10.0 mol, particularly preferably 1.2 to 10.0 mol, relative to 1 mol of the compound (61), so as to improve the yield and to reduce the waste.

The step (62) may be performed in a solvent. The solvent is preferably a water-soluble solvent, such as water, an alcohol, an ether, or a nitrile.

Examples of the alcohol include methanol, ethanol, 1-propanol, and isopropanol.

Examples of the ether include tetrahydrofuran, dioxane, and diethylene glycol diethyl ether.

Examples of the nitrile include acetonitrile, propionitrile, butyronitrile, isobutyronitrile, and benzonitrile. Acetonitrile is preferred.

The reaction temperature in the step (62) is preferably −78° C. to 200° C., more preferably −20° C. to 150° C.

The reaction pressure in the step (62) is preferably 0 to 5.0 MPa, more preferably 0.1 to 1.0 MPa.

The reaction duration in the step (62) is preferably 0.1 to 72 hours, more preferably 0.1 to 48 hours.

The compound of the invention may also suitably be produced by a production method including a step (71) of sulfuric-esterifying a compound (70) represented by the following formula:

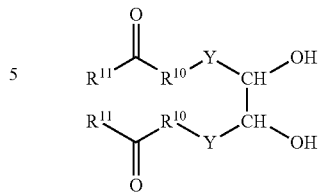

[Chem. 27]

(wherein $R^{10}$, $R^{11}$, and Y are defined as mentioned above) to provide a compound (71) represented by the following formula:

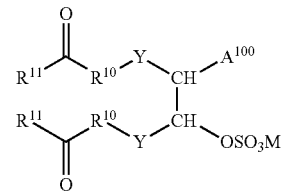

[Chem. 28]

wherein $R^{10}$, $R^{11}$, and Y are defined as mentioned above; and $A^{100}$ is —OH or —OSO$_3$M, wherein M is defined as mentioned above.

The sulfuric-esterification in the step (71) may be performed by reacting the compound (70) and a sulfating agent. Examples of the sulfating agent include sulfur trioxide amine complexes such as a sulfur trioxide pyridine complex, a sulfur trioxide trimethylamine complex, and a sulfur trioxide triethylamine complex, sulfur trioxide amide complexes such as a sulfur trioxide dimethylformamide complex, sulfuric acid-dicyclohexylcarbodiimide, chlorosulfuric acid, concentrated sulfuric acid, and sulfamic acid. The amount of the sulfating agent used is preferably 0.5 to 10 mol, more preferably 0.5 to 5 mol, still more preferably 0.7 to 4 mol, relative to 1 mol of the compound (70). One or both of the two —OH groups in the compound (20) can be sulfuric-esterified by adjusting the amount of the sulfating agent used.

The sulfuric-esterification in the step (71) may be performed in a solvent. The solvent is preferably an organic solvent, such as an ether, a halogenated hydrocarbon, an aromatic hydrocarbon, pyridine, dimethyl sulfoxide, sulfolane, or a nitrile.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

Examples of the nitrile include acetonitrile, propionitrile, butyronitrile, isobutyronitrile, and benzonitrile. Acetonitrile is preferred.

The sulfuric-esterification temperature in the step (71) is preferably −78° C. to 200° C., more preferably −20° C. to 150° C.

The sulfuric-esterification pressure in the step (71) is preferably 0 to 10 MPa, more preferably 0.1 to 5 MPa.

The sulfuric-esterification duration in the step (71) is preferably 0.1 to 72 hours, more preferably 0.1 to 48 hours.

The compound (70) may also be produced by a production method including:

a step (101) of hydroxylating a compound (100) represented by the following formula:

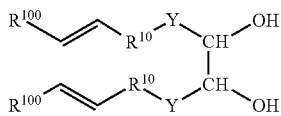

(wherein $R^{10}$ and Y are defined as mentioned above; and $R^{100}$ is an alkyl group) to provide a compound (101) represented by the following formula:

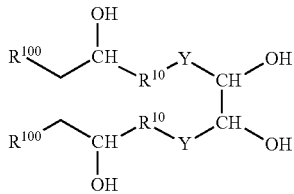

(wherein $R^{10}$, $R^{100}$, and Y are defined as mentioned above); and a step (102) of oxidizing the compound (101) to provide the compound (70).

The alkyl group for $R^{100}$ constitutes the aforementioned $R^{11}$ in the form of $R^{100}$—$CH_2$—.

The hydroxylation in the step (101) may be performed by a method (1) in which iron(II) phthalocyanine (Fe(Pc)) and sodium borohydride are allowed to act on the compound (100) in an oxygen atmosphere or a method (2) in which isopinocampheylborane ($IpcBH_2$) is allowed to act on the compound (100) and then the resulting intermediate (dialkyl borane) is oxidized.

In the method (1), iron(II) phthalocyanine may be used in a catalytic amount, and may be used in an amount of 0.001 to 1.2 mol relative to 1 mol of the compound (100).

In the method (1), sodium borohydride may be used in an amount of 0.5 to 20 mol relative to 1 mol of the compound (100).

The reaction in the method (1) may be performed in a solvent. The solvent is preferably an organic solvent, such as an ether, a halogenated hydrocarbon, an aromatic hydrocarbon, a nitrile, or a nitrogen-containing polar organic compound.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

Examples of the nitrile include acetonitrile, propionitrile, butyronitrile, isobutyronitrile, and benzonitrile. Acetonitrile is preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

The reaction temperature in the method (1) is preferably −78° C. to 200° C., more preferably 0° C. to 150° C.

The reaction pressure in the method (1) is preferably 0 to 5.0 MPa, more preferably 0.1 to 1.0 MPa.

The reaction duration in the method (1) is preferably 0.1 to 72 hours, more preferably 0.1 to 48 hours.

In the method (2), isopinocampheylborane may be used in an amount of 0.1 to 10.0 mol relative to 1 mol of the compound (100).

The reaction of the compound (100) and isopinocampheylborane may be performed in a solvent. The solvent is preferably an organic solvent, such as an ether, a halogenated hydrocarbon, or an aromatic hydrocarbon.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The temperature for the reaction of the compound (100) and isopinocampheylborane is preferably −78° C. to 200° C., more preferably 0° C. to 150° C.

The pressure for the reaction of the compound (100) and isopinocampheylborane is preferably 0 to 5.0 MPa, more preferably 0.1 to 1.0 MPa.

The duration of the reaction of the compound (100) and isopinocampheylborane is preferably 0.1 to 72 hours, more preferably 0.1 to 48 hours.

The oxidation in the method (2) may be performed by allowing an oxidizing agent to act on the intermediate. An example of the oxidizing agent is hydrogen peroxide. The oxidizing agent may be used in an amount of 0.7 to 10 mol relative to 1 mol of the intermediate.

The oxidation in the method (2) may be performed in a solvent. Examples of the solvent include water, methanol, and ethanol. Water is preferred.

The oxidation temperature in the method (2) is preferably −78° C. to 150° C., more preferably 0° C. to 100° C., still more preferably 10° C. to 80° C.

The oxidation pressure in the method (2) is preferably 0 to 5.0 MPa, more preferably 0.1 to 1.0 MPa.

The oxidation duration in the method (2) is preferably 0.1 to 72 hours, more preferably 0.1 to 48 hours.

The oxidation of the compound (101) in the step (102) may be performed by, for example, (a) a method of using the Jones reagent ($CrO_3/H_2SO_4$) (Jones oxidation), (b) a method of using Dess-Martin periodinane (DMP) (Dess-Martin oxidation), (c) a method of using pyridinium chlorochromate (PCC), (d) a method of allowing a bleaching agent (about 5% to 6% aqueous solution of NaOCl) to act in the presence of a nickel compound such as $NiCl_2$, or (e) a method of allowing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (102) may be performed in a solvent. The solvent is preferably any of water and organic solvents, such as water, ketones, ethers, halogenated hydrocarbons, aromatic hydrocarbons, and nitriles.

Examples of the ketones include acetone, methyl ethyl ketone, methyl isobutyl ketone, cyclohexanone, and diacetone alcohol. Acetone is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the aromatic hydrocarbons include benzene, toluene, and xylene. Benzene and toluene are preferred.

Examples of the nitriles include acetonitrile, propionitrile, butyronitrile, isobutyronitrile, and benzonitrile. Acetonitrile is preferred.

The oxidation temperature in the step (102) is preferably −78° C. to 200° C., and may appropriately be selected in accordance with the method used.

The oxidation pressure in the step (102) is preferably 0 to 5.0 MPa, and may appropriately be selected in accordance with the method used.

The oxidation duration in the step (102) is preferably 0.1 to 72 hours, and may appropriately be selected in accordance with the method used.

The compound (70) may also be produced by a production method including a step (201) of ozonolysis of a compound (200) represented by the following formula:

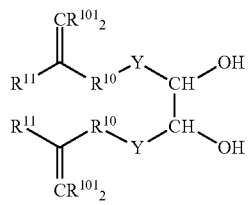

[Chem. 31]

(wherein $R^{10}$, $R^{11}$, and Y are defined as mentioned above; and $R^{101}$ is an organic group) to provide the compound (70).

$R^{101}$ is preferably a C1-C20 alkyl group. The four $R^{101}$s may be the same as or different from each other.

The ozonolysis in the step (201) may be performed by allowing ozone to act on the compound (200), followed by post-treatment with a reducing agent.

The ozone may be generated by dielectric barrier discharge in oxygen gas.

Examples of the reducing agent used in the post-treatment include zinc, dimethyl sulfide, thiourea, and phosphines. Phosphines are preferred.

The ozonolysis in the step (201) may be performed in a solvent. The solvent is preferably any of water and organic solvents, such as water, alcohols, carboxylic acids, ethers, halogenated hydrocarbons, and aromatic hydrocarbons.

Examples of the alcohols include methanol, ethanol, 1-propanol, and isopropanol. Methanol and ethanol are preferred.

Examples of the carboxylic acids include acetic acid and propionic acid. Acetic acid is preferred.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The ozonolysis temperature in the step (201) is preferably −78° C. to 200° C., more preferably 0° C. to 150° C.

The ozonolysis pressure in the step (201) is preferably 0 to 5.0 MPa, more preferably 0.1 to 1.0 MPa.

The ozonolysis duration in the step (201) is preferably 0.1 to 72 hours, more preferably 0.1 to 48 hours.

The compound (70) may also be produced by a production method including:

a step (301) of epoxidizing a compound (300) represented by the following formula:

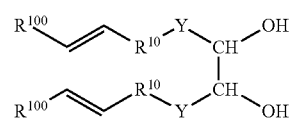

[Chem. 32]

(wherein $R^{10}$ and Y are defined as mentioned above; and $R^{100}$ is an alkyl group) to provide a compound (301) represented by the following formula:

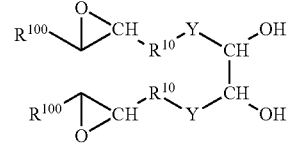

[Chem. 33]

(wherein $R^1$, $R^{100}$, and Y are defined as mentioned above);

a step (302) of reacting the compound (301) and lithium dialkyl copper represented by the formula: $R^{102}_2CuLi$ (wherein $R^{102}$ is an alkyl group) to provide a compound (302) represented by the following formula:

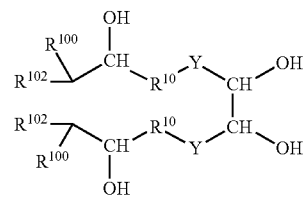

[Chem. 34]

(wherein $R^{10}$, $R^{100}$, $R^{102}$, and Y are defined as mentioned above); and a step (303) of oxidizing the compound (302) to provide the compound (70).

The alkyl groups for $R^{100}$ and $R^{102}$ constitute the aforementioned $R^{11}$ in the form of $R^{100}R^{102}$—CH—.

The two $R^{100}$s may be the same as or different from each other. The two $R^{102}$s may be the same as or different from each other.

The epoxidation in the step (301) may be performed by allowing an epoxidizing agent to act on the compound (300).

Examples of the epoxidizing agent include peroxy acids such as meta-chloroperbenzoic acid (m-CPBA), perbenzoic acid, hydrogen peroxide, and tert-butyl hydroperoxide, dimethyl dioxolane, and methyl trifluoromethyl dioxolane. Peroxy acids are preferred, and meta-chloroperbenzoic acid is more preferred.

The epoxidizing agent may be used in an amount of 0.5 to 10.0 mol relative to 1 mol of the compound (300).

The epoxidation in the step (301) may be performed in a solvent. The solvent is preferably an organic solvent, such as a ketone, an ether, a halogenated hydrocarbon, an aromatic hydrocarbon, a nitrile, pyridine, a nitrogen-containing polar organic compound, or dimethyl sulfoxide. Dichloromethane is preferred.

Examples of the ketone include acetone, methyl ethyl ketone, methyl isobutyl ketone, cyclohexanone, and diacetone alcohol. Acetone is preferred.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

Examples of the nitrile include acetonitrile, propionitrile, butyronitrile, isobutyronitrile, and benzonitrile. Acetonitrile is preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

The epoxidation temperature in the step (301) is preferably −78° C. to 200° C., more preferably −40° C. to 150° C.

The epoxidation pressure in the step (301) is preferably 0 to 5.0 MPa, more preferably 0.1 to 1.0 MPa.

The epoxidation duration in the step (301) is preferably 0.1 to 72 hours, more preferably 0.1 to 48 hours.

In the step (302), the lithium dialkyl copper may be used in an amount of 0.5 to 10.0 mol relative to 1 mol of the compound (301).

The reaction in the step (302) may be performed in a solvent. The solvent is preferably an organic solvent, such as an ether, a halogenated hydrocarbon, or an aromatic hydrocarbon.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The reaction temperature in the step (302) is preferably −78° C. to 200° C., more preferably −40° C. to 150° C.

The reaction pressure in the step (302) is preferably 0 to 5.0 MPa, more preferably 0.1 to 1.0 MPa.

The reaction duration in the step (302) is preferably 0.1 to 72 hours, more preferably 0.1 to 48 hours.

The oxidation of the compound (302) in the step (303) may be performed by, for example, (a) a method of using the Jones reagent ($CrO_3/H_2SO_4$) (Jones oxidation), (b) a method of using Dess-Martin periodinane (DMP) (Dess-Martin oxidation), (c) a method of using pyridinium chlorochromate (PCC), (d) a method of allowing a bleaching agent (about 5% to 6% aqueous solution of NaOCl) to act in the presence of a nickel compound such as $NiCl_2$, or (e) a method of allowing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (303) may be performed in a solvent. The solvent is preferably any of water and organic solvents, such as water, ketones, alcohols, ethers, halogenated hydrocarbons, aromatic hydrocarbons, and nitriles.

Examples of the ketones include acetone, methyl ethyl ketone, methyl isobutyl ketone, cyclohexanone, and diacetone alcohol. Acetone is preferred.

Examples of the alcohols include methanol, ethanol, 1-propanol, and isopropanol. Methanol and ethanol are preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the aromatic hydrocarbons include benzene, toluene, and xylene. Benzene and toluene are preferred.

Examples of the nitriles include acetonitrile, propionitrile, butyronitrile, isobutyronitrile, and benzonitrile. Acetonitrile is preferred.

The oxidation temperature in the step (303) is preferably −78° C. to 200° C., and may appropriately be selected in accordance with the method used.

The oxidation pressure in the step (303) is preferably 0 to 5.0 MPa, and may appropriately be selected in accordance with the method used.

The oxidation duration in the step (303) is preferably 0.1 to 72 hours, and may appropriately be selected in accordance with the method used.

The compound (70) may also be produced by a production method including a step (401) of oxidizing a compound (400) represented by the following formula:

[Chem. 35]

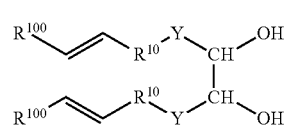

(wherein $R^{10}$ and Y are defined as mentioned above; and $R^{100}$ is an alkyl group) to provide the compound (70).

The oxidation in the step (401) may be performed by allowing an oxidizing agent to act on the compound (400) in the presence of water and a palladium compound.

Examples of the oxidizing agent include monovalent or divalent copper salts such as copper chloride, copper acetate, copper cyanide, and copper trifluoromethanethiolate, iron salts such as iron chloride, iron acetate, iron cyanide, iron trifluoromethanethiolate, and hexacyanoferrates, benzoquinones such as 1,4-benzoquinone, 2,3-dichloro-5,6-dicyano-1,4-benzoquinone, tetrachloro-1,2-benzoquinone, and tetrachloro-1,4-benzoquinone, $H_2O_2$, $MnO_2$, $KMnO_4$, $RuO_4$, m-chloroperbenzoic acid, and oxygen, and any combination of these. Copper salts, iron salts, and benzoquinones are preferred, and copper chloride, iron chloride, and 1,4-benzoquinone are more preferred.

The oxidizing agent may be used in an amount of 0.001 to 10 mol relative to 1 mol of the compound (400).

The water may be used in an amount of 0.5 to 1000 mol relative to 1 mol of the compound (400).

An example of the palladium compound is palladium dichloride. The palladium compound may be used in a catalytic amount, and may be used in an amount of 0.0001 to 1.0 mol relative to 1 mol of the compound (400).

The oxidation in the step (401) may be performed in a solvent. Examples of the solvent include water, esters, aliphatic hydrocarbons, aromatic hydrocarbons, alcohols, carboxylic acids, ethers, halogenated hydrocarbons, nitrogen-containing polar organic compounds, nitriles, dimethyl sulfoxide, and sulfolane.

Examples of the esters include ethyl acetate, butyl acetate, ethylene glycol monomethyl ether acetate, and propylene glycol monomethyl ether acetate (PGMEA, also known as 1-methoxy-2-acetoxypropane). Ethyl acetate is preferred.

Examples of the aliphatic hydrocarbons include hexane, cyclohexane, heptane, octane, nonane, decane, undecane, dodecane, and mineral spirits. Cyclohexane and heptane are preferred.

Examples of the aromatic hydrocarbons include benzene, toluene, and xylene. Benzene and toluene are preferred.

Examples of the alcohols include methanol, ethanol, 1-propanol, and isopropanol.

Examples of the carboxylic acids include acetic acid and propionic acid. Acetic acid is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the nitriles include acetonitrile, propionitrile, butyronitrile, isobutyronitrile, and benzonitrile. Acetonitrile is preferred.

The oxidation temperature in the step (401) is preferably −78° C. to 200° C., more preferably −20° C. to 150° C.

The oxidation pressure in the step (401) is preferably 0 to 10 MPa, more preferably 0.1 to 5.0 MPa.

The oxidation duration in the step (401) is preferably 0.1 to 72 hours, more preferably 0.1 to 48 hours.

The compound (100), the compound (300), and the compound (400) each may be produced by a production method including a step (501) of allowing a reducing agent to act on an aldehyde represented by the following formula:

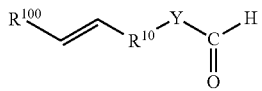

[Chem. 36]

(wherein $R^{10}$ and Y are defined as mentioned above; and $R^{100}$ is an alkyl group) to provide the compound (100).

In the step (501), a reductive coupling reaction occurs to dimerize the aldehyde, and thereby the compound (100), the compound (300), or the compound (400) is generated. Examples of the reducing agent used in the step (501) include samarium diiodide, titanium dichloride, vanadium trichloride, titanium tetrachloride, bis(cyclooctadiene) nickel, copper, magnesium, zinc, sodium, cerium trichloride, chromium oxide, and triphenyltin hydride. These reducing agents may be used in combination. The amount of the reducing agent used is preferably 0.001 to 10 mol, more preferably 0.01 to 5 mol, still more preferably 0.1 to 2 mol, relative to 1 mol of the aldehyde.

The reaction in the step (501) may be performed in a solvent. The solvent is preferably an organic solvent, more preferably an ether, a halogenated hydrocarbon, pyridine, a nitrile, an aromatic hydrocarbon, or the like.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the nitrile include acetonitrile, propionitrile, butyronitrile, isobutyronitrile, and benzonitrile. Acetonitrile is preferred.

Examples of the aromatic hydrocarbon include benzene, toluene, and xylene. Benzene and toluene are preferred.

The reaction in the step (501) is preferably performed in the presence of an alcohol. Examples of the alcohol include methanol, ethanol, and isopropanol.

The reaction temperature in the step (501) is preferably −78° C. to 200° C., more preferably −20° C. to 100° C.

The reaction pressure in the step (501) is preferably 0 to 5.0 MPa, more preferably 0.1 to 1.0 MPa.

The reaction duration in the step (501) is preferably 0.1 to 72 hours, more preferably 0.1 to 48 hours.

In any of the production methods described above, the resulting compounds may be subjected to any of evaporation of a solvent or operations such as distillation and purification after the respective steps, whereby the purity of each compound may be increased. For the resulting compounds in which M is H, such as those containing —COOH, —SO$_3$H, or —OSO$_3$H, the compounds may be brought into contact with an alkali such as sodium carbonate or ammonia so that such a group may be converted into the form of a salt.

The compound (12), the compound (21), the compound (32), the compound (41), the compound (51), the compound (62), and the compound (71) are novel compounds.

EXAMPLES

The invention is described hereinbelow with reference to examples. Still, these examples are not intended to limit the invention.

Example 1

A reactor was charged with 4-oxopentanoic acid (50.8 g), methylene chloride, and a catalytic amount of N,N-dimethylformamide (DMF). A solution of oxalyl chloride (58.3 g) in methylene chloride was dropwise added thereto at room temperature under stirring, and the components were further stirred at room temperature. After the stirring was completed, the solvent was distilled off. Thereby, 58.5 g of 1,4-dichloro-1,4-dioxobutane-2,3-diyl bis(4-oxopentanoate) was obtained at a yield of 90%.

Then, 1,4-dichloro-1,4-dioxobutane-2,3-diyl bis(4-oxopentanoate) (15.0 g), tartaric acid (5.0 g), and concentrated sulfuric acid (0.14 g) were added to the reactor and stirred at 75° C. The reaction mixture generated was recrystallized, whereby 8.9 g (yield 77%) of 2,3-bis((4-oxopentanoyl)oxy) succinic acid, which is a precursor of the target product, was obtained.

To a solution of this 2,3-bis((4-oxopentanoyl)oxy)succinic acid (173 mg) in methanol (MeOH) was dropwise added 2 M NH₃ in MeOH (0.5 ml) under cooling, and the components were stirred. Then, the solvent was distilled off at room temperature under reduced pressure, whereby 185 mg of the target ammonium salt was obtained in the form of white solid.

Example 2

A reactor was charged with 5-methoxy-5-oxopentanoic acid (25.0 g) and a catalytic amount of DMF. Thionyl chloride (40.7 g) was dropwise added thereto using a dropping funnel at room temperature. After the stirring was completed, O,O'-(1,4-dichloro-1,4-dioxobutane-2,3-diyl) dimethyl diglutarate was synthesized at a yield of 90% using an evaporator.

Then, O,O'-(1,4-dichloro-1,4-dioxobutane-2,3-diyl) dimethyl diglutarate (5.22 g), tartaric acid (2.38 g), and sulfuric acid were added using the reactor, and the components were stirred at 70° C. After the stirring, the product was purified. Thereby, 2,3-bis((5-methoxy-5-oxopentanoyl)oxy)succinic acid, which is the target product, was obtained at a yield of 52%.

Then, 2,3-bis((5-methoxy-5-oxopentanoyl)oxy)succinic acid (3.23 g) and MeOH were added to the reactor and stirred, and 2 M NH₃ in MeOH (7.95 mL) was dropwise added thereto at room temperature. After stirring, the product was dried. Thereby, the target ammonium salt was obtained at a yield of 90%.

Example 3

A reactor was charged with tartaric acid (19.1 g) and MeOH, and the components were stirred. Thionyl chloride (79.1 g) was dropwise added thereto at room temperature. After the stirring, the solvent was distilled off. Thereby, dimethyl tartrate was obtained at a yield of 93%.

Then, dimethyl tartrate (4.0 g), succinic anhydride (4.49 g), and pyridine (3.54 g) were added to the reactor and stirred at 100° C. After the stirring, toluene was added thereto. A solid precipitate was collected by filtering. The solid precipitate was then vacuum-dried.

Thereby, 4,4'-((1,4-dimethoxy-1,4-dioxobutane-2,3-diyl)bis(oxy))bis(4-oxobutanoic acid) was obtained at a yield of 86%.

Example 4

A reactor was charged with levulinic acid chloride (6.2 g), malic acid (5.0 g), and a catalytic amount of concentrated sulfuric acid, and the components were stirred at 70° C. for 12 hours. A solid reaction mixture generated was then purified. Thereby, 3.9 g (yield 45%) of 2-((4-oxopentanoyl)oxy)succinic acid was obtained.

To a solution of this 2-((4-oxopentanoyl)oxy)succinic acid (186 mg) in MeOH was dropwise added 2 M NH₃ in MeOH (0.8 ml). The components were stirred, and then the solvent was distilled off under reduced pressure. Thereby, 210 mg of the target ammonium salt was obtained in the form of white solid.

Example 5

A reactor was charged with diethyl tartrate (8.24 g), N-acetylethylenediamine (2.2 eq.), and ethanol, and the components were stirred at room temperature. Acetone was added thereto and the mixture was filtered. Thereby, an intermediate (N1,N4-bis(2-acetamidoethyl)-2,3-dihydroxysuccinamide) was obtained (9.4 g, 74%). Then, the intermediate (1.0 g) and acetonitrile were added to the reactor, and chlorosulfonic acid (8 eq.) was dropwise added thereto in an ice bath. The components were stirred at room temperature and then filtered. Thereby, a sulfo product was obtained. Water was added thereto, and then sodium carbonate was added thereto. The components were stirred at room temperature and the product was concentrated. Thereby, sodium 2,7,10,15-tetraoxo-3,6,11,14-tetraazahexadecane-8,9-diyl bis(sulfate) was obtained (1.0 g, 30%).

Example 6

A mixture of 10-undecenal (1.1 g), tetrahydrofuran (THF) (100 mL), methanol (1 mL), and a 0.1 M solution of samarium iodide (90 mL) were stirred at room temperature for two hours. Then, 100 mL of a hydrochloric acid (1 M) solution was added thereto and the mixture was extracted with diethyl ether. Then, the solvent was distilled off and the residue was purified by column chromatography, whereby docosa-1,21-diene-11,12-diol (1.0 g) was obtained. The resulting docosa-1,21-diene-11,12-diol showed the following spectrum data.

¹H-NMR (CDCl₃) δ ppm: 1.08 (J=6.8, m, 10H), 1.32 (m, 2H), 1.45 (m, 2H), 1.98 (s, 3H), 2.33 (J=7.6, t, 2H), 3.83 (J=6.5, t, 2H)

A mixture of docosa-1,21-diene-11,12-diol (16 g), 1,4-benzoquinone (10.2 g), DMF (160 mL), water (16 mL), and PdCl₂ (0.34 g) was heated and stirred at 90° C. for 12 hours.

The solvent was then distilled off under reduced pressure. The resulting residue was subjected to liquid separation with a 1 M solution of NaOHaq in toluene, and the organic phase was extracted. The solvent was then distilled off under reduced pressure and the residue was purified by column chromatography. Thereby, 11,12-dihydroxydocosa-2,21-diol (15.4 g) was obtained. The resulting 11,12-dihydroxydocosa-2,21-diol showed the following spectrum data.

¹H-NMR (CDCl₃) δ ppm: 1.29-1.49 (m, 14H), 2.08 (s, 3H), 2.45 (J=7.6, t, 2H), 3.51 (J=6.5, t, 2H)

A mixture of 11,12-dihydroxydocosa-2,21-diol (13 g), a sulfur trioxide triethylamine complex (13.9 g), and tetrahydrofuran (140 mL) was stirred at 50° C. for 12 hours. A solution of sodium methoxide (3.8 g) in methanol was dropwise added to the reaction solution.

A solid precipitate was filtered under reduced pressure. Thereby, sodium 2,21-dioxodocosa-11,12-diyl bis sulfate (15.5 g) was obtained. The resulting sodium 2,21-dioxodocosa-11,12-diyl bis sulfate showed the following spectrum data.

¹H-NMR (CDCl₃) δ ppm: 1.08 (J=6.8, m, 10H), 1.32 (m, 2H), 1.45 (m, 2H), 1.98 (s, 3H), 2.33 (J=7.6, t, 2H), 3.83 (J=6.5, t, 2H)

Example 7

An ammonium salt of 2,3-bis((6-methoxy-6-oxohexanoyl)oxy)succinic acid was synthesized in the same manner as in Example 2, except that 6-methoxy-6-oxohexanoic acid was used instead of 5-methoxy-5-oxopentanoic acid.

Example 8

An ammonium salt of 2,3-bis((8-methoxy-8-oxooctanoyl)oxy)succinic acid was synthesized in the same manner as in Example 2, except that 8-methoxy-8-oxooctanoic acid was used instead of 5-methoxy-5-oxopentanoic acid.

Example 9

A mixture of an ammonium salt of 2-((6-methoxy-6-oxohexanoyl)oxy)-3-((8-methoxy-8-oxooctanoyl)oxy)succinic acid, an ammonium salt of 2,3-bis((6-methoxy-6-oxohexanoyl)oxy)succinic acid, and an ammonium salt of 2,3-bis((8-methoxy-8-oxooctanoyl)oxy)succinic acid was synthesized in the same manner as in Example 2, except that 5-methoxy-5-oxopentanoic acid was changed to 6-methoxy-6-oxohexanoic acid and 8-methoxy-8-oxooctanoic acid.

Example 10

A reactor was charged with dimethyl L-aspartate hydrochloride (8.1 g), succinic anhydride (5.0 g), triethylamine (12.2 g), and dichloromethane, and the components were stirred at room temperature. Liquid separation and recrystallization were then performed. Thereby, 4-((1,4-dimethoxy-1,4-dioxobutan-2-yl)amino)-4-oxobutanoic acid was obtained at a yield of 22%.

Example 11

A three-neck flask was charged with 11-hydroxy-undecan-2-one (587 mg, 3.15 mmol) and toluene (4 ml), and the components were stirred. Fumaryl chloride (241 mg, 1.58 mmol) was then dropwise added thereto at room temperature.

The components were heated and stirred at 80° C. for three hours. After the reaction was completed, the toluene solvent was distilled off using an evaporator. Thereby, the target product in the form of diester was obtained at a yield of 89% (637.8 mg, 1.41 mmol).

Next, $NaHSO_3$ (529 mg, 5.08 mmol) and $EtOH/H_2O/THF=20$ ml/20 ml/10 ml were added to the three-neck flask and stirred. The diester (767 mg, 1.69 mmol) was dissolved in 10 ml of THF, and this solution was dropwise added thereto at room temperature.

The reaction solution was stirred under reflux for three hours. The reaction solution was then concentrated using an evaporator and the concentrated product was purified by column chromatography. Thereby, sodium 1,4-dioxo-1,4-bis((10-oxoundecyl)oxy)butane-2-sulfate (824 mg) was obtained at a yield of 88% (824 mg, 1.48 mmol).

Example 12

A sodium salt of 12-hydroxy-2,21-dioxodocosan-11-yl hydrogen sulfate was obtained in the same manner as in Example 6, except that the amount of the sulfur trioxide triethylamine complex was changed from 13.9 g to 6.9 g.

Example 13

Sodium 1,4-dioxo-1,4-bis((10-oxopentyl)oxy)butane-2-sulfate was synthesized in the same manner as in Example 11, except that 5-hydroxypentan-2-one was used instead of 11-hydroxy-undecan-2-one.

Example 14

Sodium 1,4-dioxo-1,4-bis((6-oxoheptyl)oxy)butane-2-sulfate was synthesized in the same manner as in Example 11, except that 7-hydroxyheptan-2-one was used instead of 11-hydroxy-undecan-2-one.

Example 15

To a solution of 48 g of 6-hepten-1-ol in 128 ml of DMF and in 26 ml of water were added 46 g of p-benzoquinone and 1.5 g of palladium chloride, and the components were heated at 75° C. for 1.5 hours. The reaction solution was separated and the organic layer was concentrated. The resulting crude product was evaporated under reduced pressure and purified. Thereby, 15 g (yield 26%) of 7-hydroxy-heptan-2-one was obtained. A solution of 3 g of 4-cyclohexene-1,2-dicarbonyl dichloride in 10 ml of THF was ice-cooled. A solution of 3.8 g of 7-hydroxyheptan-2-one in 15 ml of dehydrated THF was added thereto, and then 2.9 g of triethylamine was slowly added thereto. The components were left to stand for one hour, and then stirred at room temperature for six hours. The reaction mixture liquid was separated and concentrated. The resulting crude product was then purified. Thereby, 4.1 g (yield 50%) of bis-(6-oxoheptyl) 4-cyclohexene-1,2-dicarboxylate was obtained. To a solution of 1.8 g of bis-(6-oxoheptyl) 4-cyclohexene-1,2-dicarboxylate in 27 ml of water and in 27 ml of acetone were added 3.5 ml of 60% aqueous sulfuric acid and 2.9 g of potassium permanganate under ice cooling. While the ice cooling was continued, the components were stirred for two hours. The temperature was then slowly increased, and the components were stirred at room temperature for 12 hours. A precipitate was filtered off. The filtrate was then separated and concentrated. Thereby, 1.7 g of dicarboxylic acid was obtained. This crude product was suspended in 3 ml of water and 6.8 ml of 1 N KOH aqueous solution was added thereto. The mixture was concentrated under reduced pressure. The resulting crude product was then purified. Thereby, 0.96 g (yield 39%) of the target potassium dicarboxylate, i.e., potassium 3,4-bis-(6-oxoheptyloxycarbonyl)-hexanedioate was obtained.

Experimental Examples

Each of the compounds obtained in the examples was dissolved in water so as to give the concentration shown in Table 1, and the surface tension thereof was determined. The surface tension was determined by the Wilhelmy method at 20° C. The results are shown in Table 1.

TABLE 1

| | | Amount of compound relative to water (wt %) | | |
|---|---|---|---|---|
| | | 0.01 | 0.1 | 1.0 |
| Surface tension (mN/m) | Example 1 | 72.0 | 72.1 | 68.5 |
| | Example 2 | 72.1 | 72.4 | 69.0 |
| | Example 3 | 72.8 | 71.7 | 67.2 |
| | Example 4 | 72.5 | 72.1 | 69.8 |
| | Example 5 | 72.9 | 72.7 | 72.5 |
| | Example 6 | 61.0 | 50.7 | 46.1 |
| | Example 7 | 72.7 | 71.3 | 62.7 |
| | Example 8 | 70.6 | 54.1 | 40.1 |
| | Example 9 | 72.0 | 66.5 | 55.0 |
| | Example 10 | 72.0 | 71.5 | 69.2 |
| | Example 11 | 60.8 | 48.6 | 47.7 |
| | Example 12 | 69.0 | 53.0 | 50.0 |
| | Example 13 | 73.7 | 65.0 | Slightly soluble |
| | Example 14 | 69.4 | 57.4 | Slightly soluble |
| | Example 15 | 73.4 | 69.8 | 62.5 |

INDUSTRIAL APPLICABILITY

The compound of the invention can favorably reduce the surface tension of water.

The compound of the invention can suitably be used as a surfactant.

The compound of the invention can suitably be used as a surfactant promoter (in particular, a surfactant promoter for agents such as coating material, lacquer, and adhesive).

The compound of the invention can suitably be used as a viscosity reducing agent, for example.

The compound of the invention can suitably be used as a dispersant, in particular an aqueous dispersant, for example.

The compound of the invention can suitably be used as an emulsifier, for example.

The invention claimed is:

1. A compound represented by the following formula (1):

[Chem. 1]
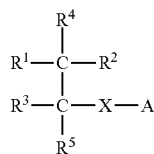

wherein $R^1$ to $R^5$ are each H or a monovalent substituent;
at least one of $R^1$ or $R^3$ is a group represented by the formula: —Y—$R^6$; and at least one of $R^2$ or $R^5$ is a group represented by the formula: —X-A or a group represented by the formula: —Y—$R^6$;
Xs at the respective appearances are the same as or different from each other, and are each a divalent linking group or a direct bond;
As at the respective appearances are the same as or different from each other, and are each —COOM, —$SO_3$M, or —$OSO_3$M, wherein M is H, a metal atom, $NR^7_4$, imidazolium optionally containing a substituent, pyridinium optionally containing a substituent, or phosphonium optionally containing a substituent, wherein $R^7$ is H or an organic group;
$R^6$s at the respective appearances are the same as or different from each other, and are each
a group represented by the formula: —$R^{10}$—CO—$R^{11}$,
a group represented by the formula: —$R^{10}$—C(=O)O—$R^{11}$,
a group represented by the formula: —$R^{11}$, or
a group represented by the formula: —$R^{10}$—$NR^8$CO—$R^{11}$,
wherein $R^8$ is H or an organic group; $R^{10}$ is an alkylene group; and $R^{11}$ is an alkyl group optionally containing a substituent;
the group represented by the formula: —Y—$R^6$ is
a group represented by the formula: —$R^{10}$—CO—$R^{11}$ where Y is a direct bond,
a group represented by the formula: —OC(=O)—$R^{10}$—CO—$R^{11}$ where Y is —OC(=O)—,
a group represented by the formula: —C(=O)O—$R^{10}$—CO—$R^{11}$ where Y is —C(=O)O—,
a group represented by the formula: —OC(=O)—$R^{10}$—C(=O)O—$R^{11}$ where Y is —OC(=O)—,
a group represented by the formula: —C(=O)O—$R^{11}$ where Y is —C(=O)O—,
a group represented by the formula: —$NR^8$CO—$R^{10}$—CO—$R^{11}$ where Y is —$CONR^8$—, or
a group represented by the formula: —$CONR^8$—$R^{10}$—$NR^8$CO—$R^{11}$ where Y is —$NR^8$CO—,
wherein $R^8$ is H or an organic group, $R^{10}$ is an alkylene group, and $R^{11}$ is an alkyl group optionally containing a substituent, and when two or more of the groups represented by the formula: —Y—$R^6$ are present, the groups at the respective appearances are the same as or different from each other;
$R^4$ and $R^5$ are each H or a C1-C4 alkyl group;
any two of $R^1$ to $R^5$ optionally bind to each other to form a ring;
when $R^6$ contains none of a carbonyl group, an ester group, and an amide group, X is a divalent linking group containing at least one selected from the group consisting of a carbonyl group, an ester group, an amide group, and a sulfonyl group.

2. The compound according to claim 1,
wherein the compound is a compound represented by the following formula (1-1):

[Chem. 2]

wherein $R^3$ to $R^6$, X, A, Y, and —Y—$R^6$ are defined as mentioned above, or a compound represented by the following formula (1-2):

[Chem. 3]

wherein $R^4$ to $R^6$, X, A, Y, and —Y—$R^6$ are defined as mentioned above.

3. The compound according to claim 1,
wherein M is H, Na, K, Li, or $NH_4$.

4. The compound according to claim 1,
wherein M is Na, K, or $NH_4$.

5. The compound according to claim 1,
wherein M is $NH_4$.

6. A surfactant comprising the compound according to claim 1.

7. An aqueous dispersant comprising the compound according to claim 1.

* * * * *